United States Patent [19]

Sirimanne et al.

[11] Patent Number: 5,163,911

[45] Date of Patent: Nov. 17, 1992

[54] OVER-THE-WIRE CATHETER

[75] Inventors: D. Laksen Sirimanne, Huntington Beach; Sandra L. Cutter, Mission Viejo; Zohrab S. Kemkemian, West Covina, all of Calif.; Peter D. Heijer, Botanicuslaan 15, 9571 AA Haren, Netherlands; Paul M. Teirstein, 402 Coast Blvd. S., La Jolla, Calif. 92037

[73] Assignees: Baxter International Inc.; Peter Den Heijer; Paul S. Teirstein, Deerfield, Ill.

[21] Appl. No.: 863,525

[22] Filed: Apr. 3, 1992

Related U.S. Application Data

[63] Continuation of Ser. No. 608,110, Oct. 31, 1990, abandoned.

[51] Int. Cl.⁵ ............................................. A61M 29/02
[52] U.S. Cl. ..................................... 604/164; 128/772
[58] Field of Search .................. 604/164, 96; 128/772, 128/657

[56] References Cited

U.S. PATENT DOCUMENTS

| | | | |
|---|---|---|---|
| 33,166 | 2/1990 | Samson . | |
| 3,552,384 | 1/1971 | Pierie et al. | 128/657 |
| 4,490,421 | 12/1984 | Levy . | |
| 4,540,404 | 9/1985 | Wolvek . | |
| 4,545,390 | 10/1985 | Leary | 128/772 |
| 4,573,470 | 3/1986 | Samson et al. | 128/772 |
| 4,615,472 | 10/1986 | Nash | 128/657 |
| 4,616,653 | 10/1986 | Samson et al. . | |
| 4,619,263 | 10/1986 | Frisbie et al. | 128/772 |
| 4,757,827 | 7/1988 | Buchbinder et al. | 128/657 |
| 4,763,667 | 8/1988 | Manzo | 604/164 |
| 4,790,331 | 12/1988 | Okada et al. | 128/772 |
| 4,846,174 | 7/1989 | Willard et al. . | |
| 4,957,117 | 9/1990 | Wysham | 128/772 |
| 4,960,411 | 10/1990 | Buchbinder | 128/657 |
| 5,045,061 | 9/1991 | Seifert et al. . | |

FOREIGN PATENT DOCUMENTS 0244955 11/1987 European Pat. Off. .

Primary Examiner—Paul J. Hirsch
Attorney, Agent, or Firm—Walter A. Hackler; Michael C. Schiffer; Debra D. Condino

[57] ABSTRACT

A catheter system includes a guide wire, a working catheter and a torque device for removably coupling the working catheter to the guide wire while enabling rotation of the guide wire to the working catheter. Advancement of the guide wire in a vascular system is enabled by rotating the guide wire while the working catheter is coupled thereto. A procedure for use of the catheter system includes the simultaneous insertion of the guide wire and working catheter into a vascular system and independent rotation of the guide wire for steering the guide wire, with working catheter coupled thereto, through the vascular system.

6 Claims, 2 Drawing Sheets

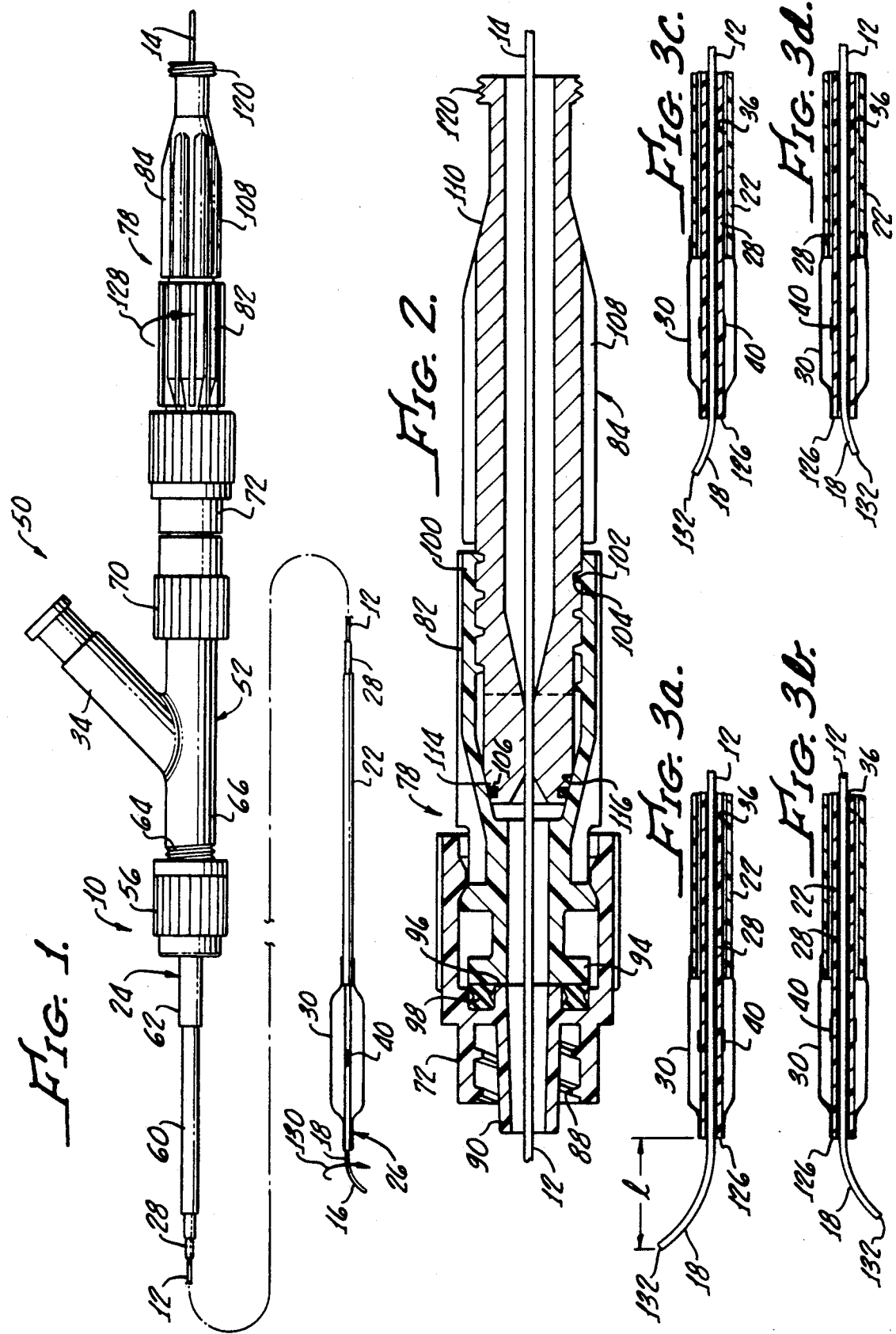

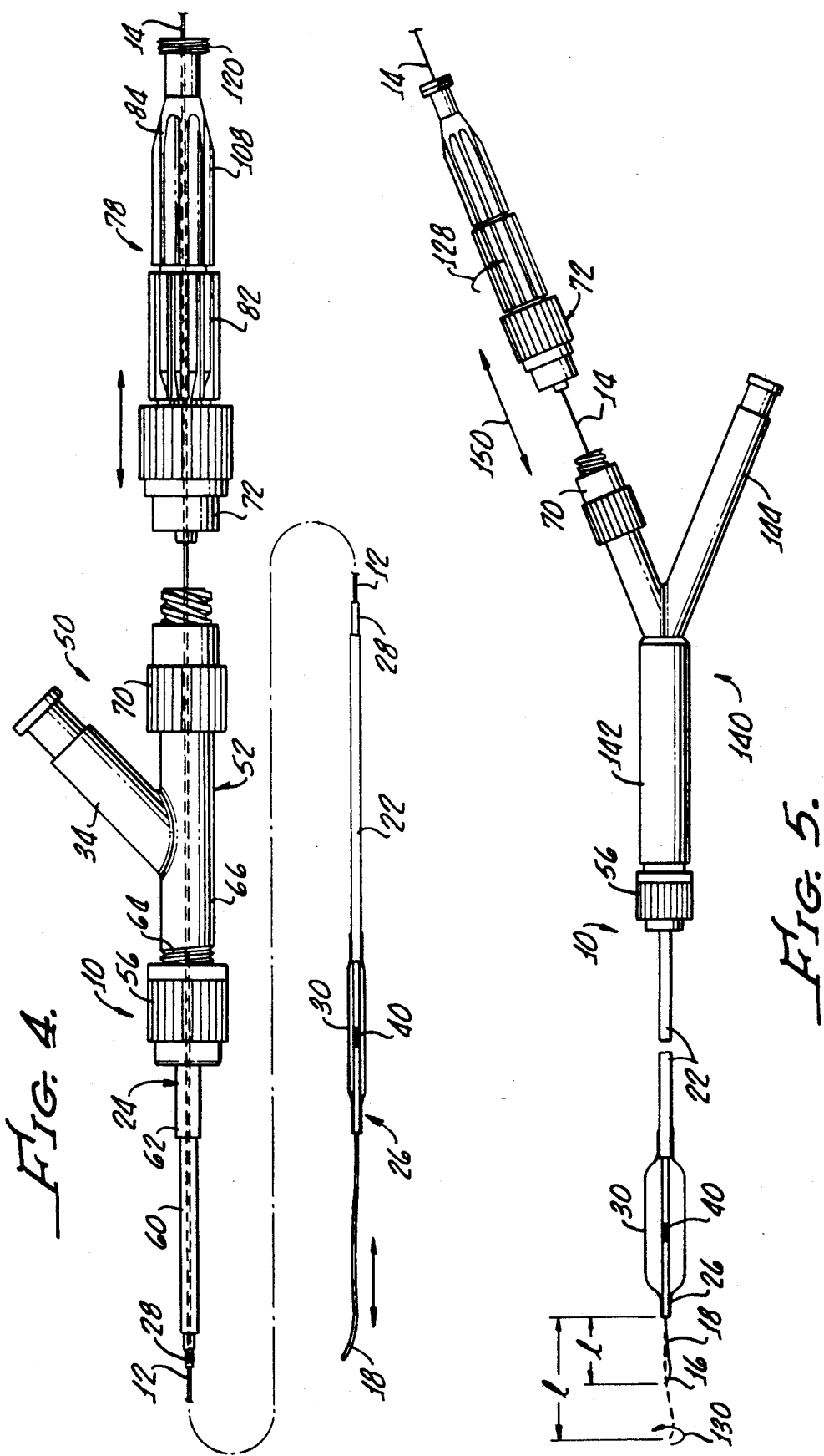

OVER-THE-WIRE CATHETER

This is a continuation of application Ser. No. 07/608,110 filed on Oct. 31, 1990 now abandoned.

BACKGROUND OF THE INVENTION

The invention generally relates to a catheter system for performing transluminal angioplasty procedures and the like and is more particularly directed to a steerable dilatation catheter having advantages not found in conventional "fixed wire" catheters or "over-the-wire" catheters.

A number of vascular conditions may be treated by percutaneous transluminal coronary angioplasty in which a balloon catheter is routed through the vascular system and positioned across a stenotic lesion. The balloon is then inflated with a fluid to compress the lesion against the artery wall in order to increase its effective luminal diameter.

Apparatus suitable for such procedures currently available can be classified as either a "fixed wire" catheter system or an "over-the-wire" catheter system. A typical "fixed wire" catheter system such as described in U.S. Pat. No. 33,166, dated Feb. 20, 1990, includes a guide wire with a dilatation, or working, catheter permanently fixed thereto. The distinctive advantage of this type of catheter is its relatively low profile, or small overall outer diameter, which enables its use in smaller arteries and in situations with more advanced stenosis in which an artery may be closed to such an extent that a larger diameter catheter, such as an over-the-wire catheter, may not be suitable.

The fixed wire catheter system is not without disadvantage. Because the dilatation catheter is fixed to the guide wire at a distal end thereof which includes a flexible steering portion or tip, the tip itself is necessarily fixed, as well as it's length, thus limiting the steerability of the fixed wire catheter. In addition, since the fixed wire dilatation catheter system must be rotated, both the wire and the balloon are is subject to distortion, particularly "balloon wrapping", due to the rotation thereof which may result in non-uniform inflation, limited ability or even inability for inflation and deflation thereof.

In addition, with a fixed wire system the working catheter cannot be replaced over the guide wire which can be left in situ to establish an established path through the vascular system as hereinafter described.

An over-the-wire catheter system, such as described in U.S. Pat. No. 4,540,404, utilizes a separate guide wire. The guide wire may first be inserted into a vascular system, and thereafter, a dilatation, or working, catheter may be inserted thereover, until a balloon member thereof is positioned across the stenotic lesion. Advantageously, because the guide wire is not fixed to the working catheter, the guide wire and working catheter may be inserted and withdrawn independent of each other. Thus, if necessary, the guide wire can be manipulated independently through a particularly curvaceous artery. In addition, once the guide wire is in place, the working catheter may be replaced as may be required to change it for a working catheter with a different or larger balloon during the angioplasty procedure. In view of these advantages, the over-the-wire system has been considered more "user friendly" than a fixed wire system.

Similarly, because the guide wire may be independently inserted and removed from a vascular system, if a change in a tip shape, size or type is deemed necessary to facilitate advancement or access, the guide wire may be removed, leaving the working catheter in place which subsequently provides an open channel for the replacement guide wire. Once the guide wire is positioned past the stenotic lesion, the working catheter can then be positioned to place the balloon portion across the stenotic lesion for inflation. After deflation and removal of the working catheter, the guide wire may be left in place, enabling reinsertion or exchange of the balloon catheter if necessary for a repeated angioplasty procedure. Alternatively, if the guide wire is removed leaving the working catheter, the lumen thereof, through which the guide wire had passed, is now available for monitoring or other uses.

The present invention is directed to a fixable wire catheter having a number of advantages, not available in prior art devices, as will hereinafter be described in greater detail.

SUMMARY OF THE INVENTION

A catheter system in accordance with the present invention includes a working catheter adapted for sliding along a guide wire within a vascular system. Means are provided for enabling the working catheter to be inserted and moved within the vascular system with the guide wire and further enabling the guide wire to be rotated within the working catheter during advancement of the guide wire for steering the guide wire therethrough. This arrangement allows simultaneous insertion of the guide wire and working catheter without rotation of the latter, which rotation could result in damage to or distortion of the working catheter, such as "balloon wrapping" as hereinbefore described.

A catheter system in accordance with the present invention may also include a guide wire sized for insertion into an animal vascular system and having a proximal and a distal end. The distal end includes a means for advancing the guide wire through the vascular system which more particularly may include a flexible, yet shapable, end portion.

The means provided for enabling rotation of the guide wire within the working catheter allows the orientation and re-orientation of the shapable flexible end portion to positions suitable for advancing the guide wire, with the working catheter coupled thereto, through the vascular system.

The means for removably coupling the working catheter to the guide wire may include a compressible member having an opening therethrough which provides means for enabling passage of the guide wire and fluid therethrough when the compressible member is not compressed and the guide wire has not been inserted.

An advantage of the present invention is the control of the length of the guide wire tip portion extending beyond the working catheter caused by the relative longitudinal placement of the distal end of the guide wire with respect to the distal end of the working catheter.

DESCRIPTION OF THE DRAWINGS

A better understanding of the present invention may be had in connection with the following detailed description, taken in conjunction with the accompanying drawings, in which:

FIG. 1 is a side view of the catheter system in accordance with the present invention generally showing a guide wire, a working catheter, a Y-connector, and a torquing device unit to couple the working catheter to the guide wire as hereinafter described in greater detail;

FIG. 2 is a cross-sectional view of the torquing device in accordance with the present invention;

FIGS. 3a, b, c, and d are diagrammatic illustrations of relative positions of the distal end of the guide wire having a shapable portion thereon, and the distal end of the working catheter showing how the working catheter may enable the steering of the guide wire in accordance with the present invention;

FIG. 4 is a side view of the catheter system shown in FIG. 1 with the torquing device separated from the Y-connector, enabling independent longitudinal movement of the guide wire within the catheter; and FIG. 5 is a side view of the present invention including an alternative standard type Y connector and showing how manipulation of the guide wire within the working catheter is enabled when a torquing device is decoupled from the Y connector.

DETAILED DESCRIPTION

Turning now to FIG. 1, there is shown a catheter system 10, including a guide wire 12, having a proximal end 14 and a distal end 16, the latter having a shapable flexible end portion 18 thereon, which may be of any suitable configuration, such as a fine, helically wound coiled wire or the like, and a working catheter 22 having a proximal end 24, a distal end 26, and an inside diameter 28.

Disposed at the distal end 26 of the working catheter 22 is an inflatable balloon 30 in a fluid communication with a port 34 via a working catheter lumen 36. The configuration of the working catheter 22, including balloon 30, as well as the guide wire 12, may be of any conventional design as is well known in the art. In addition, as is also well known in the art, a radiopaque marker 40 may be provided for use in determining the position of the distal end 26 of the working catheter 22 as it is advanced through a vascular system (not shown).

As shown in FIG. 1, control apparatus 50 may be provided which includes a Y-connector 52, including the port 34 which provides means for inflating and deflating the balloon 30 by injecting or aspirating a fluid through the lumen 36 of the working catheter 22. The Y-connector 52, as well as a coupling 56 joining the working catheter 22 thereto, may be of conventional design. In addition, as shown in FIG. 1, the outside diameter of the working catheter 22 may be in creased in portions 60, 62 by the use of elastomeric coatings or metallic or polymeric sheathings for stiffening purposes to enhance the strength thereof.

It can be appreciated that when the coupling 56 is attached, for example by means of threads 64, to the Y-connector body 66, the working catheter 22 is mounted in a non-rotatable relationship with the control apparatus 50. The guide wire 12, however, extending through the control apparatus 50, including couplings 70, adapter 72 and a torquing device 78, is rotatable within the working catheter 22 as will be explained hereinafter in greater detail.

Turning now to FIG. 2, there is shown in cross-section the torquing device 78, which is part of the control apparatus 50, generally showing the adapter 72, along with a sleeve 82, and a shaft 84.

The adapter includes internal threads 88 for engagement with the coupling 70 of the control apparatus and including a lumen 90 therethrough for communication with the lumen 28 of the working catheter 22.

Disposed within the adapter 72 for rotation therein is a sleeve head 94, having a face 96 pressed against a seal 98 for facilitating rotation.

The sleeve 82 includes a body 100 having threads 102 adapted for engagement with mating threads 104 on the shaft 84. When engaged, a seal 106 is pressed against the sleeve 94 to prevent a fluid which may be present in lumen 90 from passing therepast.

Ribs 108 on a body portion 110 facilitate the screwing of the shaft 84 into the sleeve 82 for compressing a compressible member, or tip 114, as it is forced against a tapered side diameter 116 of the sleeve 82, thus compressing the tip 114 onto the wire 12 and forming a seal for fluids within the lumen 90. Hence, it can be seen that the shaft 84 and the sleeve 82 and adapter 72 provide means for coupling the working catheter 22 to the guide wire 12 and also means for enabling rotation of the guide wire 12 within the working catheter 22. It is to be appreciated that since the working catheter 22 is affixed to the Y-coupling 52 along with the adapter 72, when the tip 114 is compressed against the guide wire 12, longitudinal sliding motion of the guide wire is prevented, but rotation within the working catheter 22 is made possible.

A luer thread 120 is provided on the body portion 110 and disposed in fluid communication with a central passage 122 of the shaft 84, which enables fluid to pass therethrough and into the lumen 90 of the adapter 72 and lumen 28 of the working catheter 22 for flushing or other purposes.

Referring now to FIG. 1, working catheter 22, in operation, may be slid over the guide wire 12 until a selected length of the shapable flexible end portion 18 extends beyond a working catheter tip 126, see FIGS. 3a, b, c and d. At that point, the working catheter 22 is removably coupled to the guide wire 12 by rotation, or twisting, of the shaft 84 into the sleeve 82, thereby compressing the tip 114 onto the guide wire 12. The working catheter guide wire 12 is then inserted into a vascular system as in a conventional "fixed wire" system and thereafter, rotation of the sleeve 82, as shown by the arrow 128 (FIG. 1), results in the rotation of the guide wire 12 within the working catheter 22 and the shapable flexible end portion 18 as shown by the arrow 130. This provides means for orienting and reorienting the shapable flexible end portion 18 to positions suitable for advancement of the guide wire 12 with the working catheter 22 coupled thereto, through the vascular system (not shown).

The shapable flexible end portion 18 includes a length thereof "1", which is determined by the relative longitudinal placement of a distal end tip 132 with respect to the distal tip 126 of the working catheter 22 as shown in FIG. 3a. FIG. 3b shows the same length, 1, with the guide wire 12 end portion 18 oriented 180° from the orientation shown in FIG. 3a. Such orientations facilitate the advancement and manipulation of the guide wire 12 and working catheter 22 through the vascular system.

As shown in FIGS. 3c and 3d, the working catheter 22 may be clamped to the guide wire 12 at a position at which the longitudinal placement of the distal tip 132 of the guide wire 12 with respect to the distal tip 126 of the working catheter 22 is substantially shorter, as may be necessary to facilitate advancement of the guide wire 12, with the working catheter 22 attached thereto, through various arcuate portions of the vascular system.

Turning to FIGS. 4 and 5, there is shown the torquer 72 decoupled with the Y-connector 52 and an alternative Y-connector 140 having a body 142 and port 144 for fluid access to the collector lumen 36 for inflating and deflating the balloon 30.

The torquing device 78 is shown decoupled to the Y-connectors 52, 140 in FIGS. 4 and 5. In this configuration the guide wire 14 may be moved in a sliding fashion within the working catheter 22 as indicated by the arrow 150, which results in adjusting the length, 1, of guide wire 12 projecting beyond the working catheter distal tip 126. In this manner the guide wire 14 may be advanced within a vascular system ahead of the working catheter 22. Alternatively, when the torquing device 70 is coupled to either of the Y-members 52, 140, the working catheter 22 may be advanced with or, manipulated with, the guide wire 12.

In accordance with the present invention, a procedure for the insertion of a working catheter 22 through a vascular system includes the steps of inserting the guide wire 12, having the shapable end portion 18 into a vascular system (not shown). The shapable flexible end portion is used to direct, or steer, the guide wire 12 through the arcuate and bifurcated portions of the vascular system. Thereafter, the working catheter 22 is inserted over the guide wire 12 and coupled to the guide wire 12 with a selectable length, 1, of the shapable flexible end portion 18 protruding from the working catheter 22.

Alternatively, the working catheter 22 may be disposed over the guide wire 12 and coupled thereto as hereinabove described before simultaneous insertion of the guide wire 12 and working catheter into the vascular system.

Thereafter, the guide wire 12 may be rotated within the working catheter 22 in order to orient the shapable flexible end portion to a position suitable for continued advancement of the guide wire 12 with the working catheter coupled thereto within the vascular system (see FIGS. 3a, b, c and d). With the proper orientation, the procedure then includes advancing the guide wire 12 and working catheter 22 in the vascular system.

Although there has been hereinabove described a specific arrangement of a flexible over-the-wire catheter system in accordance with the present invention, for the purpose of illustrating the manner in which the invention may be used to advantage, it will be appreciated that the invention is not limited thereto. Accordingly, any and all modifications, variations, or equivalent arrangements which may occur to those skilled in the art should be considered to be within the scope of the invention as defined in the appended claims.

What is claimed is:

1. A catheter system for use with a guide wire having a proximal and a distal end, said catheter system comprising:
    a working catheter adapted for sliding over said guide wire within a vascular system;
    a torquing device including means, removably coupling said torquing device to the guide wire, for rotating the guide wire within the working catheter and for sliding the guide wire within the working catheter; and
    coupling means for removably coupling said torquing device with the working catheter to prevent sliding therebetween without limiting rotatability of the guide wire within the working catheter.

2. The catheter system according to claim 1 wherein said torquing device and coupling means are disposed near the guide wire proximal end.

3. The catheter system according to claim 2 wherein said torquing device includes a compressible member having means, defining an opening, for enabling passage of said guide wire and fluid therethrough when said compressible member is not compressed onto the guide wire.

4. A catheter system comprising:
    a guide wire having a proximal and a distal end, said distal end including means for enabling steering of said guide wire through a vascular system by rotation of the guide wire therein; a working catheter adapted for sliding over said guide wire within the vascular system;
    a torquing device including means, removably coupling said torquing device to the guide wire, for rotating the guide wire within the working catheter and for sliding the guide wire within the working catheter; and
    coupling means for removably coupling said torquing device with the working catheter to prevent sliding therebetween without limiting rotatability of the guide wire within the working catheter.

5. The catheter system according to claim 4 wherein said torquing device and coupling means are disposed near the guide wire proximal end.

6. The catheter system according to claim 5 wherein said torquing device includes a compressible member having means, defining an opening, for enabling passage of said guide wire and fluid therethrough when said compressible member is not compressed onto the guide wire.

* * * * *